United States Patent
Yu et al.

(10) Patent No.: US 8,999,446 B2
(45) Date of Patent: Apr. 7, 2015

(54) METHODS FOR ADJUSTING ADHESION STRENGTH DURING SENSOR PROCESSING

(75) Inventors: Ying Yu, Singapore (SG); TienChoy Loh, Singapore (SG); ShianYeu Kam, Singapore (SG)

(73) Assignee: STMicroelectronics Pte Ltd., Singapore (SG)

( * ) Notice: Subject to any disclaimer, the term of this patent is extended or adjusted under 35 U.S.C. 154(b) by 339 days.

(21) Appl. No.: 13/544,865

(22) Filed: Jul. 9, 2012

(65) Prior Publication Data

US 2014/0010962 A1    Jan. 9, 2014

(51) Int. Cl.
  *B05D 3/10* (2006.01)
  *B05D 5/02* (2006.01)
  *C03C 17/32* (2006.01)
  *G01N 33/487* (2006.01)

(52) U.S. Cl.
  CPC ............ *C03C 17/32* (2013.01); *G01N 33/4875* (2013.01); *G01N 2203/0091* (2013.01)

(58) Field of Classification Search
  CPC ...... B05D 1/005; B05D 3/002; B05D 3/0254; B05D 3/104
  USPC ............ 427/307, 309, 389.7, 240; 216/39, 97
  See application file for complete search history.

(56) References Cited

U.S. PATENT DOCUMENTS 5,108,819 A  *  4/1992  Heller et al. ................ 428/195.1
2005/0142321 A1 * 6/2005  Miyahara et al. ............ 428/64.2

* cited by examiner

*Primary Examiner* — Kirsten Jolley
(74) *Attorney, Agent, or Firm* — Seed IP Law Group PLLC

(57) ABSTRACT

The present disclosure is directed to systems and methods for adjusting adhesion strength between materials during semiconductor sensor processing. One or more embodiments are directed to using various surface treatments to a substrate to adjust adhesion strength between the substrate and a polymer. In one embodiment, the surface of the substrate is roughened to decrease the adhesive strength between the substrate and the polymer. In another embodiment, the surface of the substrate is smoothed to increase the adhesive strength between the substrate and the polymer.

20 Claims, 3 Drawing Sheets

METHODS FOR ADJUSTING ADHESION STRENGTH DURING SENSOR PROCESSING

BACKGROUND

1. Technical Field

The present disclosure is directed to systems and methods for adjusting adhesion strength between a sensor and a substrate.

2. Description of the Related Art

During sensor fabrication, in some types of devices the sensor is processed while attached to a substrate. The substrate acts as a carrier and provides structural and mechanical support to the sensors during subsequent processing steps. In some cases, flexible sensors are formed from a polymer film, such as polyimide, while the polymer film is attached to the substrate.

BRIEF SUMMARY

The present disclosure is directed to systems and methods for adjusting adhesion strength between materials during semiconductor sensor processing. One or more embodiments are directed to surface treating a substrate to adjust adhesion strength between the substrate and a polymer. In one embodiment, the surface of the substrate is roughened to decrease the adhesive strength between the substrate and the polymer. In another embodiment, the surface of the substrate is smoothed to increase the adhesive strength between the substrate and the polymer.

DETAILED DESCRIPTION

Figure 1:
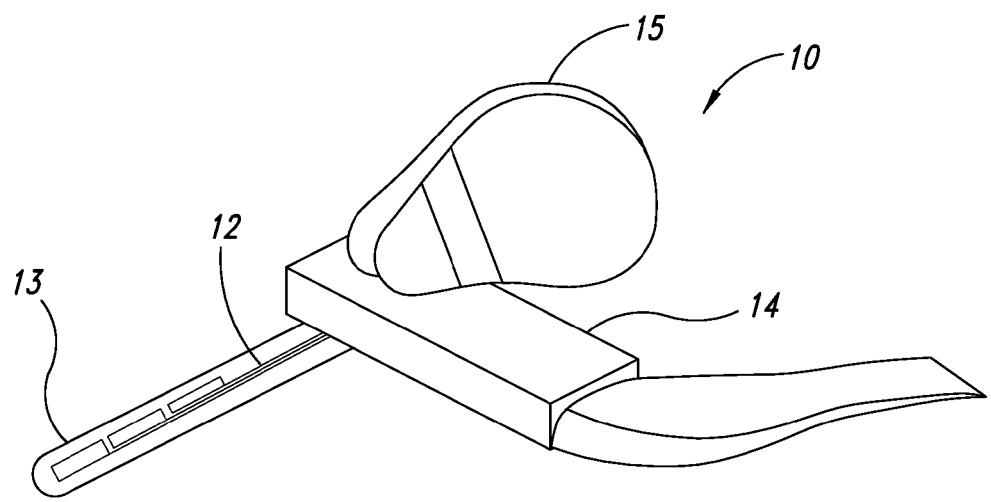
FIG. 1 is a schematic isometric view of a glucose sensor system in accordance with the present disclosure.
Figure 2:
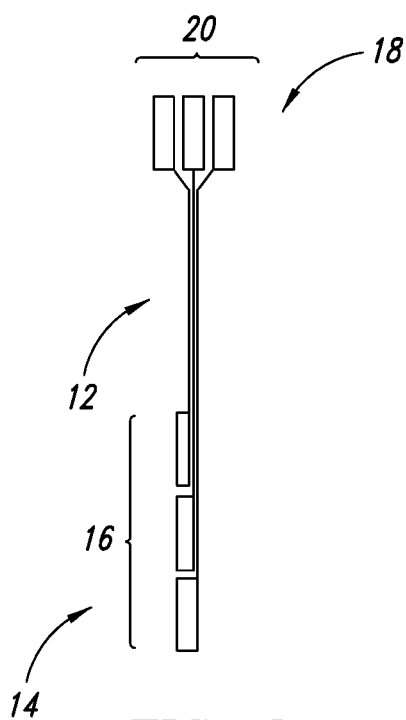
FIG. 2 is close up top view of the sensor of the glucose sensor system in FIG. 1.

FIGS. 1-2 collectively show a glucose sensor system 10 that includes a sensor 12 for measuring a person's glucose levels. The sensor 12 is mounted on an insertion support member 13 as is shown in FIG. 1. In the illustrated embodiment, the sensor 12 is a flexible bio-medical sensor, and in some embodiments may be a microelectromechanical system (MEMS) sensor. As shown in FIG. 2, a first end 14 of the sensor 12 includes sensing electrodes 16. Blood is placed in contact with the sensing electrodes 16 for sensing various levels, such as glucose levels. A second end 18 of the sensor 12 includes contact pads 20 that are electrically coupled to the sensing electrodes 16 via conductive traces. The sensing electrodes 16 may comprise a metal material, and in some embodiments, the sensing electrodes 16 comprise at least one of chrome and gold. The contact pads 20 are configured to receive signals indicative of the sensed glucose levels from sensed electrodes 16 via the traces. The glucose sensor system 10 may further include a support portion 14 for supporting the insertion support member 13 and a transmitter 15 that is configured to wirelessly provide the signals indicative of the sensed glucose levels to a monitor (not shown).

The sensor 12 is flexible in that it is deformable in response to a force applied thereto. In that regard, the sensor 12 may be formed from a flexible material, such as a polymer.

Figure 3:
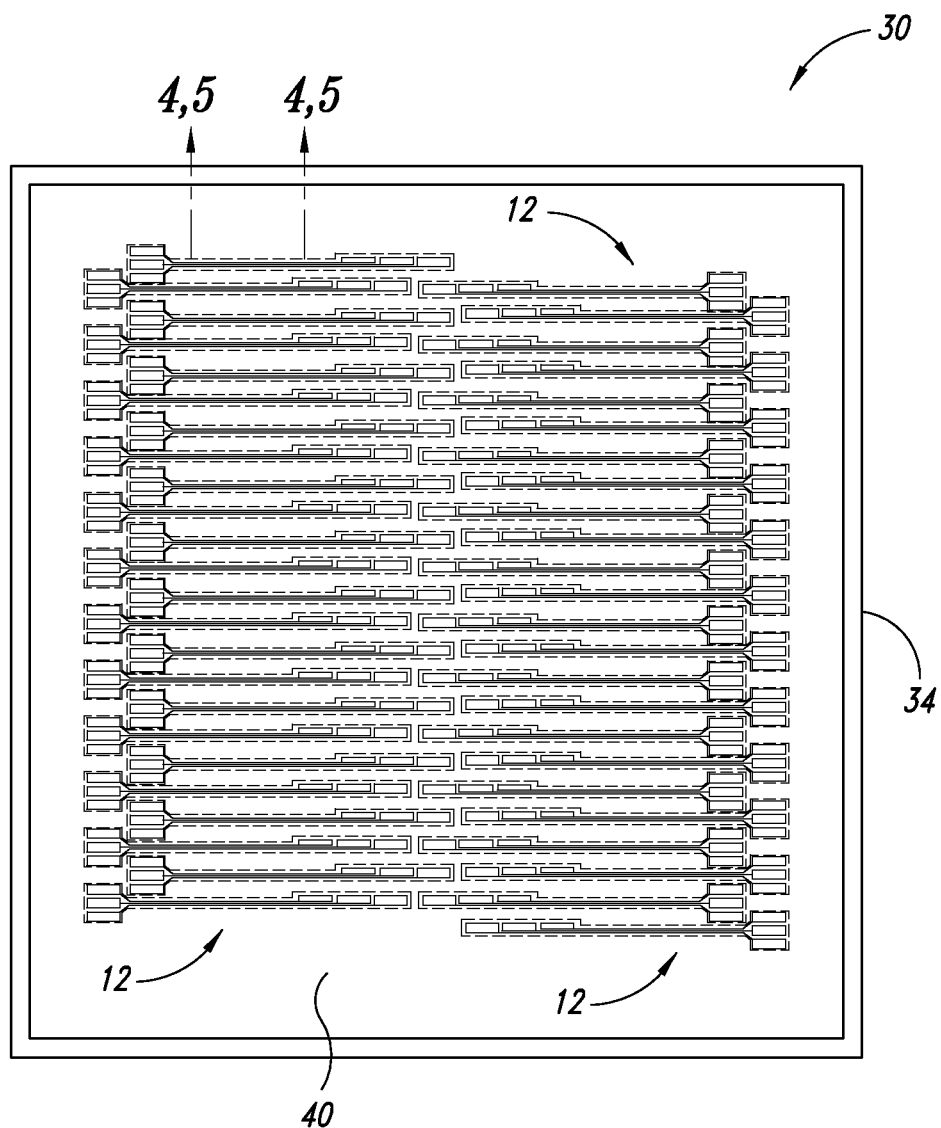
FIG. 3 is a schematic top view of a substrate having a plurality of flexible sensors thereon in accordance with the present disclosure.

FIG. 3 illustrates a slide 30 that includes a plurality of the flexible sensors 12 of FIGS. 1-2 secured to a substrate 34. The flexible sensors 12 are formed on a polymer 40 while the polymer 40 is secured to the substrate 34. The substrate 34 provides structural and/or mechanical support to the flexible sensors 12 during subsequent processing. The flexible sensors 12 are arranged on the slide 30 in spaced relation to an outer perimeter of the slide 30. The outer perimeter defines a cutting edge, in which the slide 30 was separated, such as by laser cutting, from adjacent slides on a wafer as is well known in the art. In some embodiments, portions of the polymer 40 may be removed from the substrate 34 at the perimeter of the slides 30 to define a cutting line.

Figure 4:
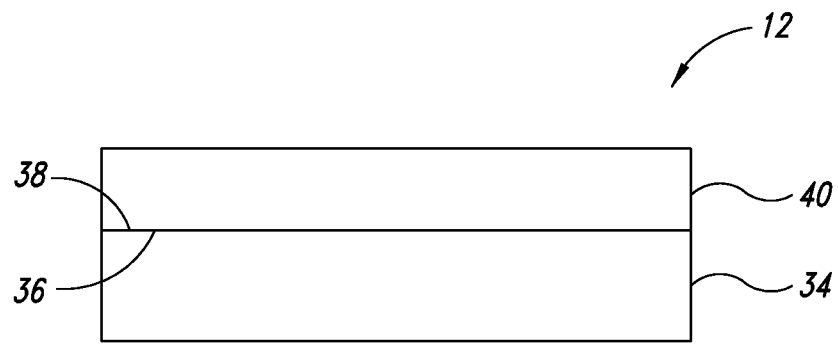
FIG. 4 is a cross section view of the FIG. 4.

FIG. 4 shows a partial cross section view of a flexible sensor 12 on the substrate 34 as shown in FIG. 3. The cross section is taken adjacent to the traces in the flexible sensor 12 electrically coupling the bond pads to the sensing electrodes to simplify the image. A lower surface 36 of the polymer 40 that forms the flexible sensors 12 is secured to a surface 38 of the substrate 34. The substrate 34 is any substrate that is suitably rigid to support the flexible sensors 12 during downstream processing. In one embodiment, the substrate 34 comprises glass, such as Alumino Silicate 1737, which is boroaluminosilicate glass. In other embodiments, the substrate 34 comprises silicon, metal or other rigid materials.

The polymer 40 used to form the flexible sensor 12 may be any polymer 40 configured to shrink during a curing or baking process. Such polymers 40 may include silicone compounds, polyimides, biocompatible solder masks, epoxy acrylate copolymers, or the like. In one embodiment, the polymer is polyimide Durimide® 116.

The polymer 40 may be deposited or formed on the substrate 34. In one embodiment, the polymer 40 is coated on the surface 38 of the substrate 34 by spin coating on the wafer. In that regard, the polymer 40 may be dispensed in a flowable form at a center portion of a wafer of which the substrate 34 is one of many that comprise the wafer; and while the wafer rotates, the polymer 40 spreads across the surface 38 of the wafer due to centripetal force. The polymer 40 is cured and the flexible sensor 12 may be formed via downstream processing.

An upper surface of the flexible sensor 12 may further include an insulation layer (not shown), such as a polymer, formed thereon. It is to be understood that the insulation layer on the upper surface of the flexible sensor 12 may having openings exposing the sensing electrodes and the bond pads discussed in reference to FIGS. 1-2. It is to be appreciated that the insulation layer on the upper surface may be a different material or the same material as the polymer 40 that forms the flexible sensor 12 and secures the flexible sensor 12 to the substrate 34.

Figure 5:
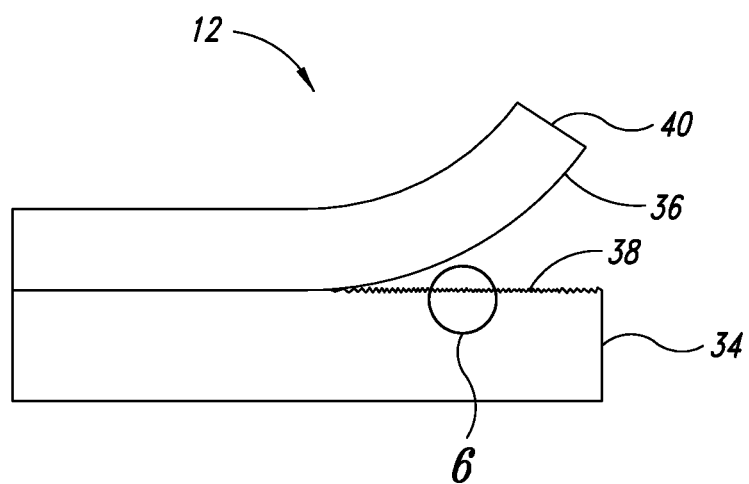
FIG. 5 is the cross section view of the FIG. 5 illustrating the removal of the flexible sensor.

After processing the flexible sensor is complete, the individual flexible sensors 12 may be removed, such as peeled as is shown in FIG. 5, from the substrate 34 and installed in a device, such as the glucose sensor system 10 of FIG. 1. In order to prevent damage to the flexible sensors 12 during the removal process, adequate control over the adhesion between the polymer 40 of the flexible sensor 12 and the substrate 34 is desired. In particular, lower adhesion may be desired such that the sensor 12 may be easily removed from the substrate 34 after downstream processing steps have been completed. In other situations, however, higher adhesion may be desired such that the sensor 12 remains adhered to the substrate 34 post downstream processing.

Previous ways for adjusting the adhesion strength between a polymer, such as polyimide, and a substrate are rather limiting. Methods for increasing the adhesive strength of polyimide includes adding an adhesive promoter or by curing the polyimide. However, these methods do not allow adequate control over the adhesive properties that may be needed for various applications. For instance, although adhesive promoters and curing are useful for increasing adhesive strength of the polyimide, they do not reduce the adhesive strength of the polyimide. Furthermore, the temperatures in which an adhesive material can exposed may be limited by properties of the adhesive, such as the materials curing temperature and glass transition temperature.

The adhesive strength of polyimide may also be adjusted (i.e. increased or decreased) by varying the thickness of the polyimide. Although this provides some control over the adhesive strength of the polyimide, semiconductor processing design rules typically defines the thickness of the polyimide, thus preventing further adjustments to the thickness to obtain the necessary adhesive properties for a particular application.

Figure 6:
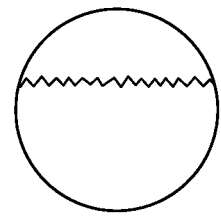
FIG. 6 is a close up view of the circle in FIG. 5.

According to embodiments of the present disclosure, prior to applying the polymer 40 to the substrate 34, the substrate 34 may be surface treated to change the surface condition of the substrate 34. In that regard, the adhesion strength between the polymer 40 and the substrate 34 may be controlled. In the illustrated embodiment, the surface 38 of the substrate 34 is roughened as can be seen in FIG. 5 as the flexible sensor 12 is peeled from the surface 38 of the substrate 34 and more clearly shown in the close up view in FIG. 6. In some embodiments, the roughened surface 38 of the substrate 34 may be achieved by etching, such as wet etching or plasma etching, the surface 38. In one embodiment, the substrate 34 is etched with sulfuric acid.

The inventors unexpectedly discovered that by changing the surface condition of the substrate 34, different adhesion strengths between the substrate 34 and the polymer 40 can be achieved. In particular, the inventors realized that by roughening the surface 38 of the substrate 34, adhesion strength between the substrate 34 and the polymer 40 is substantially reduced. It was also learned that by smoothing the surface 38 of the substrate 34, the adhesion strength between the substrate 34 and the polymer 40 may be increased.

One embodiment of the present disclosure will now be described. In this embodiment, the substrate is boro-aluminosilicate glass and a surface of the substrate was roughened via wet etch processing. The substrate will be referred to hereafter as "the treated substrate." The surface of the treated substrate was roughened using a mixture of sulfuric acid, deionized water, and hydrogen peroxide, where the mixture's temperature was increased to 130° C. After treatment, the treated substrate had an average roughness value ($R_a$) of ~1.0 nanometers and a root mean squared roughness value ($R_q$) of ~1.33 nanometers. In this embodiment, the polyimide was applied to the surface of the treated substrate to a thickness of about 20 microns ±3, the stack was cured at a temperature of 325° C. ±10 for about 30 minutes, and flexible sensors were formed thereon. The flexible sensors were then peeled from the treated substrate at a peel speed of 1 inch per minute. The adhesion strength between the polyimide and the treated substrate was determined using the following equation:

$$Wa = \frac{P_\theta(1 - \cos\theta)}{w}$$

where, Wa=the work of detachment per unit area of bonding surface; θ=peel angle; $P_\theta$=peel force; w=width of strip being peeled.

Thus, if peel angle=90°, then cos θ=0.

Therefore, $$Wa = \frac{P_\theta}{w}$$

Thus, if w=1 inch, then
Wa=$P_{90°}$

The peel force was measured to be 20 grams/force (gf) and was compared to the peel force measurement from a substrate that did not undergo surface treatment (referred to herein after as "untreated substrate"). The surface of the untreated substrate had a $R_a$ value of ~0.65 nanometers and $R_q$ value of ~0.94 nanometers. The peel force of the untreated substrate was 400 gf.

The results, over 10 times reduction in peel force for the treated substrate over the untreated substrate, were unexpected. It is generally expected that when a flowable adhesive is applied to a roughened surface, the strength of the adhesion increases because the amount of surface area in contact with the adhesive increases. That is, the adhesive flows into the peaks and valleys making up the roughed surface and thus spreads across a greater surface area, than when the surface area is substantially smooth, without peaks and valleys. In this case, however, the adhesion strength unexpectedly decreased. The inventors discovered that because the polyimide shrank during the curing process, the amount of surface contact the polyimide had with the substrate also decreased thereby reducing the adhesion strength between the polyimide and the substrate.

The various embodiments described above can be combined to provide further embodiments. These and other changes can be made to the embodiments in light of the above-detailed description. For instance, although the described embodiments are directed to flexible sensors, it is to be understood that the sensors may also be rigid. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method comprising:
   treating a surface of a substrate to increase an average roughness value of the surface of the substrate;
   applying a polymer to the surface of the substrate;
   curing the polymer in a manner that causes the polymer to shrink, wherein shrinking the polymer and roughening the surface of the substrate reduces an adhesive bond between the polymer and the surface of the substrate; and
   forming a sensor on the polymer.

2. The method of claim 1, wherein the polymer is polyimide.

3. The method of claim 2, wherein applying a polymer to the surface of the substrate comprises applying the polyimide at a center portion of the surface of the substrate and rotating the substrate.

4. The method of claim 1, wherein the substrate comprises glass.

5. The method of claim 4, wherein the glass is boro-aluminosilicate glass.

6. The method of claim 1, wherein roughening a surface of a substrate comprises etching the surface of the substrate.

7. The method of claim 6, wherein etching the surface of the substrate comprises etching the surface of the substrate with fluid.

8. The method of claim 7, wherein the fluid comprises at least one of sulfuric acid, deionized water, and hydrogen peroxide.

9. The method of claim 1, wherein forming the sensor comprises forming a flexible glucose sensor.

10. A method comprising:
   etching a surface of a glass substrate to roughen the surface;
   depositing polyimide to the roughened surface of the glass substrate, the polyimide having first dimensions;
   curing the polyimide;
   shrinking the polyimide to second dimensions when cured, wherein etching and shrinking the polyimide reduces an adhesive bond between the polymer and the surface of the substrate; and
   forming a sensor on the polyimide.

11. The method of claim 10, wherein etching the surface of the substrate comprises a etching the surface of the substrate in a fluid.

12. The method of claim 11, wherein the fluid is sulfuric acid.

13. The method of claim 10, wherein curing the polyimide comprises baking the polyimide at a temperature above 300° C.

14. The method of claim 10, wherein depositing polyimide to the roughened surface of the substrate comprises applying the polyimide at a center portion of the roughened surface and rotating the substrate.

15. The method of claim 10, wherein the glass substrate comprises boro-aluminosilicate.

16. The method of claim 10, wherein forming the sensor comprises forming a flexible sensor on the polyimide.

17. The method of claim 10, wherein the surface of the substrate has a first average roughness value, and wherein etching the surface of the glass substrate comprises etching the surface of the glass substrate so that the surface of the substrate has a second average roughness value that is greater than the first average roughness value.

18. A method comprising:
   treating a surface of a substrate that increases an average roughness value of the surface of the substrate;
   applying polyimide to the surface of the substrate;
   curing the polyimide thereby causing the polyimide to shrink, wherein shrinking the polymer and increasing the roughness of the surface of the substrate reduces an adhesion strength between the polymer and the surface of the substrate; and
   forming a sensor on an exposed surface of the polyimide.

19. The method of claim 18, wherein treating the surface of the substrate comprises roughening the surface of the substrate by etching the surface of the substrate.

20. The method of claim 18, wherein the substrate is boro-aluminosilicate glass.

* * * * *